US00PP37085P2

(12) United States Plant Patent
Evison

(10) Patent No.: US PP37,085 P2
(45) Date of Patent: Nov. 4, 2025

(54) ***CLEMATIS* PLANT NAMED 'EviGsy154'**

(50) Latin Name: ***Clematis patens* X *viticella***
Varietal Denomination: EviGsy154

(71) Applicant: Raymond J. Evison Ltd., Vale (GB)

(72) Inventor: Raymond J. Evison, Vale (GB)

(73) Assignee: RAYMOND J. EVISON LTD., Vale (GB)

( * ) Notice: Subject to any disclaimer, the term of this patent is extended or adjusted under 35 U.S.C. 154(b) by 0 days.

(21) Appl. No.: 19/194,202

(22) Filed: Apr. 30, 2025

(30) Foreign Application Priority Data

Nov. 26, 2024 (QZ) ..... PBR 20242807

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan Mccormick Ewoldt
(74) *Attorney, Agent, or Firm* — Penny J. Aguirre

(57) ABSTRACT

A new cultivar of *Clematis* plant named 'EviGsy154' that is characterized by its numerous flowers that are large in size, its flowers that stay consistently dark red in color with contrasting yellow anthers, its repeat flowering; blooming from May through July and re-blooming in late August and September, its compact plant habit, its healthy and sturdy foliage with less tendency to have yellow lower leaves, and its good suitability for use in gardens and in containers.

2 Drawing Sheets

Botanical classification: *Clematis patens* X *viticella*.
Variety denomination: 'EviGsy154'.

CROSS REFERENCE TO A RELATED APPLICATION

This application claims priority to European Community Plant Variety Office (CPVO) Plant Breeder's Rights Application No. 2024/2807 filed on Nov. 26, 2024, the entire contents of which is incorporated by reference herein.

BACKGROUND OF THE INVENTION

The present invention relates to a new and distinct cultivar of *Clematis* of hybrid origin and will be referred to hereafter by its cultivar name 'EviGsy154'. 'EviGsy154' is grown as an herbaceous climbing plant for use in the landscape or as a flowering potted plant for the terrace.

'EviGsy154' derived from an ongoing breeding program by the Inventor at his nursery in Guernsey, The Channel Islands. The goal of the breeding program is to select new cultivars of *Clematis* with a compact plant habits with an abundance of flowers that are large in size with unique flower colors. 'EviGsy154' was selected as a single unique plant in April of 2019 and arose from a controlled cross made in June of 2014 between unnamed and unpatented proprietary seedlings of *Clematis patens* X *viticella* from the Inventor's breeding program as both the female and male parents.

Asexual propagation of the new cultivar was first accomplished by stem cuttings under the direction of the Inventor in Guernsey, The Channel Islands in May of 2019. Asexual propagation by internodal stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'EviGsy154' as a unique cultivar of *Clematis*.

1. 'EviGsy154' exhibits numerous flowers that are large in size.
2. 'EviGsy154' exhibits flowers that stay consistently dark red in color with contrasting yellow anthers.
3. 'EviGsy154' exhibits repeat flowering; blooming from May through July and re-blooming in late August and September.
4. 'EviGsy154' exhibits a compact plant habit.
5. 'EviGsy154' exhibits healthy and sturdy foliage with less tendency to have yellow lower leaves.
6 'EviGsy154' exhibits good suitability for use in gardens and in containers.

The female parent of 'EviGsy154' differs from 'EviGsy154' in having a less compact plant habit flowers with brown anthers. The male parent of 'EviGsy154' differs from 'EviGsy154' in having a more compact plant habit (dwarf) and flowers with tepals that are light purple in color. 'EviGsy154' can be most closely compared to the *Clematis* cultivars 'evipo022' (not patented) and 'Evipo081' (U.S. Plant Pat. No. 31,113). 'Evipo022' is similar to 'EviGsy154' in having flowers with red tepals. 'Evipo022' differs from 'EviGsy154' in having a taller plant height, a less floriferous and non-reblooming blooming habit, and in occasionally producing semi-double flowers. 'Evipo081' is similar to 'EviGsy154' in flower coloration. 'Evipo081' differs from 'EviGsy154' in having less prolific foliage that does not hold its color under stress and flowers that are lighter red in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Raymond Evison *Clematis*, RHS Plants, Plantipp, Waitrose Garden, Crocus, Facebook, The Druys, Hayloft, Floral Daily, Telegraph Garden Shop, Waitrose Garden, Garden Centre Plants, Berns Garden Center and Landscaping, Benson Lumber & Hardware, Horticulture Week, QVC UK, Horticulture Week, and DEGA GRUNER MARKT.

BRIEF DESCRIPTION OF THE DRAWINGS

The accompanying color photographs illustrate the overall appearance and distinct characteristics of the new *Clematis*. The photographs were taken of a plant about 2-years in age as grown in a 17-cm container in a conventional greenhouse in in Guernsey, The Channel Islands.

The photograph in FIG. 1 shows a side view of a plant of 'EviGsy154' in bloom.

Figure 1:
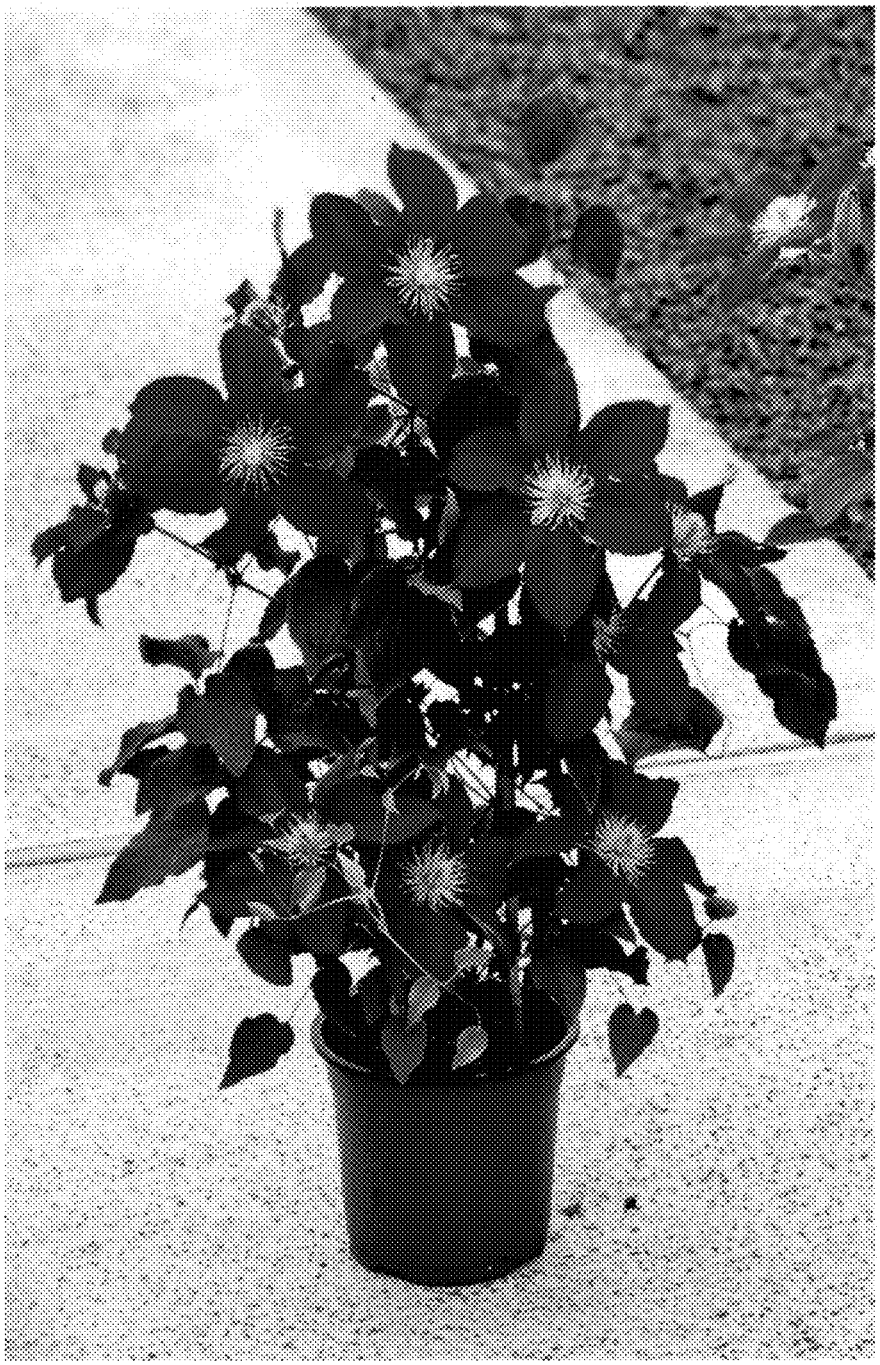
Figure 2:
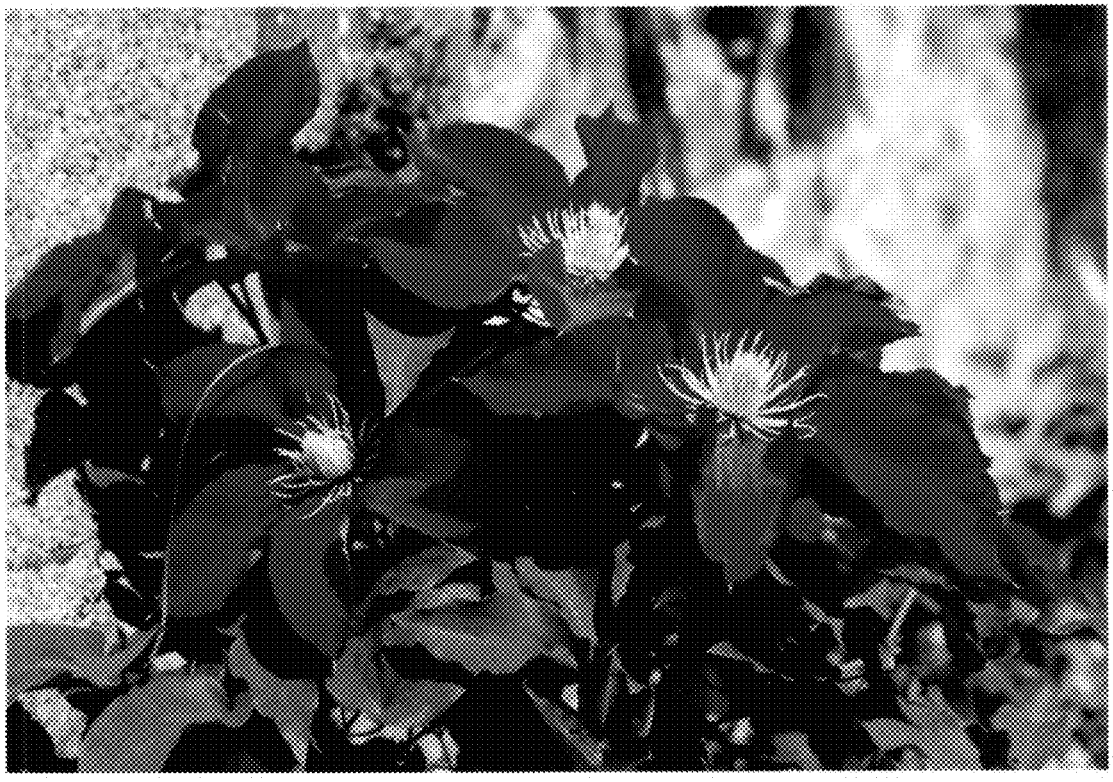

The photograph in FIG. 2 provides a close-up view of flowers of 'EviGsy154'.

Figure 3:
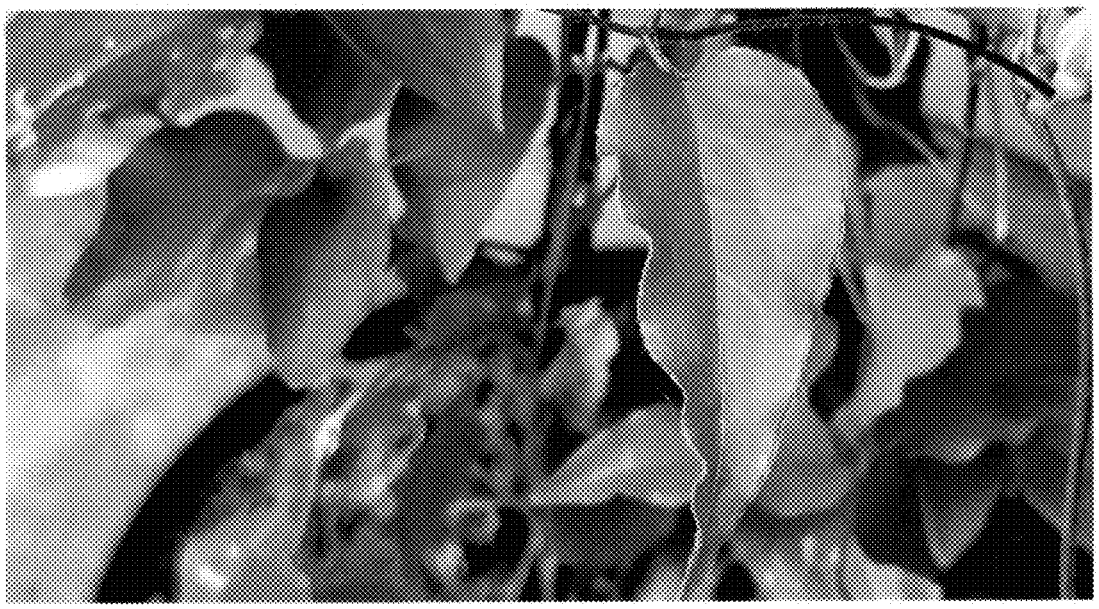

The photograph in FIG. 3 provides a close-up view of a leaf of 'EviGsy154'.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of 2.5-year-old plants of 'EviGsy154' as grown in a greenhouse in 17-cm containers in Guernsey, The Channel Islands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from May to July and reblooms in late August and September in Guernsey, The Channel Islands.

*Plant type*.—Herbaceous woody vine, early blooming large flowered *Clematis*.

*Plant habit*.—Climber, blooms on new wood but will also bloom on old wood if left unpruned, compact.

*Height and spread*.—Average of 58 cm in height and 39 cm in width as a 2.5 year-old plant grown in a container, reaches 90 cm to 1.2 m in height and width in a growing season in the landscape.

*Hardiness*.—At least in U.S.D.A. Zones 5 to 9.

*Diseases*.—No susceptibility or resistance to pests and diseases has been observed.

*Root description*.—Fleshy.

*Propagation*.—Softwood cuttings from vegetative shoots.

*Time required for root initiation*.—Roots initiate in 3 to 4 weeks, another 4 to 6 weeks to produce a fully rooted cutting ready for potting, root development from plug to P7 is 3 to 6 months, 30 weeks to mature in a P12 container.

*Growth rate*.—Moderate.

Stem description:

*Shape*.—Round.

*Stem color*.—Young; 144A, flushed with 187A to 187B mature and wood; N188C to N188D.

*Stem size*.—Length from base to flowering portion of the stem; 39 cm in length; 2 mm in width.

*Stem surface*.—Very sparsely pubescent.

*Stem strength*.—Strong.

*Internode length*.—Average of 9 cm.

*Branching*.—Basal branching, (2 main stems, 6 lateral).

Foliage description:

*Leaf arrangement*.—Opposite, ternate.

*Leaf division*.—Compound.

*Leaf attachment*.—Petiolate.

*Leaf quantity*.—18 per stem, 3 leaflets per whole leaf.

*Leaf size*.—Average of 8 cm in length and 10 cm in width.

*Leaflet shape*.—Ovate.

*Leaflet base*.—Rounded to obtuse.

*Leaflet apex*.—Acute.

*Leaflet venation*.—Palmate, color; young upper surface 144C, young lower surface 146A to 146B, mature upper surface 137A, mature lower surface 137B to 137C.

*Leaflet margins*.—Entire.

*Leaflet attachment*.—Petiolule.

*Leaflet surface*.—Upper surface glabrous, glossy, lower surface matte.

*Leaflet size*.—Average of 6 cm in length and 2.8 cm in width.

*Leaflet color*.—Young upper surface; 144A, young lower surface; 146A, mature upper surface 137B, mature lower surface 137C.

*Petioles*.—Up to 4.4 cm in length, 1 mm in width, color; 187A and 144A sparsely pubescent surface.

*Petiolules*.—Up to 1.7 cm in length, 1 mm in diameter, color; 187A and 144A sparsely pubescent surface.

Inflorescence description:

*Inflorescence type*.—Solitary.

*Inflorescence arrangement*.—On terminal and axillary nodes.

*Pedicel*.—2.8 cm in length, 2 mm in diameter, 144B in color, glabrous surface, moderate strength.

*Bud description*.—Ovoid in shape, 2 cm in length, 9 mm in width, 145A and 145C in color, pubescent surface.

*Flower fragrance*.—No.

*Lastingness of flowers*.—Long lasting; individual flowers last about 14 days, self-cleaning.

*Flower quantity*.—6 open flowers, 5 buds.

*Flower type*.—Single, rotate, spreading, star-shaped.

*Flower aspect*.—Outward, rotate, held open in a tubular shape when opening and becomes flat as they mature.

*Flower size*.—Average of 10.2 cm in diameter and 3 cm in depth.

*Tepal number*.—Average of 6.

*Tepal shape*.—Broadly elliptic.

*Tepal apex*.—Acuminate.

*Tepal base*.—Acute.

*Tepal margins*.—Entire with light undulations.

*Tepal surface*.—Both surfaces glabrous, satiny and matte.

*Tepal color*.—When opening upper surface; 59A to 59B, when opening lower surface; 145C to 145D, middle stripe and outer sides 80D and 59A to 59B, when fully open upper surface; a blend of 71A, 61A, 80B to 80C, base 72A, central stripe 80C, when fully open lower surface; 61A, central stripe N155A and N82C, base 145D.

*Tepal size*.—Average of 5 cm in length and 2.8 cm in width.

*Tepal arrangement*.—Overlapping.

*Receptacle*.—3 mm in depth, 5 mm in width, pubescent surface, round in shape, 144B in color.

Reproductive organs:

*Gynoecium*.—Pistils; between 70 and 80, style; 1.5 cm in length, 1 mm in diameter, color 145C, stigma; slightly superior relative to the length of the filaments and height of the anthers, very small and hard to see, ovary; 145A to 145B in color.

*Androecium*.—Stamens; 120, filaments; 1 cm in length, glabrous surface, NN155A and 92A in color, anthers; 7 mm in length, linear in shape, 1C in color, glabrous, pollen was not observed.

*Seed*.—Seed head; an average of 1.5 cm in length, 2.5 cm in width, shiny hairs, style; plumose at base, color; 144B and 151A, seed development was not observed.

It is claimed:

1. A new and distinct cultivar of *Clematis* plant named 'EviGsy154' as herein illustrated and described.

* * * * *